(12) United States Patent
Norton

(10) Patent No.: US 8,175,808 B2
(45) Date of Patent: May 8, 2012

(54) METHOD FOR DETERMINING DISEASE TREATMENT DURATION

(75) Inventor: Larry Norton, New York, NY (US)

(73) Assignee: Sloan Kettering Institute for Cancer Research, New York, NY (US)

( * ) Notice: Subject to any disclaimer, the term of this patent is extended or adjusted under 35 U.S.C. 154(b) by 1411 days.

(21) Appl. No.: 11/384,882

(22) Filed: Mar. 20, 2006

(65) Prior Publication Data

US 2006/0224049 A1    Oct. 5, 2006

Related U.S. Application Data

(60) Provisional application No. 60/667,509, filed on Apr. 1, 2005, provisional application No. 60/672,461, filed on Apr. 18, 2005.

(51) Int. Cl.
*G06F 19/10* (2011.01)
*G01N 33/48* (2006.01)

(52) U.S. Cl. ............................................ 702/19; 436/64

(58) Field of Classification Search .................. None
See application file for complete search history.

(56) References Cited

U.S. PATENT DOCUMENTS 6,871,171 B1 *  3/2005  Agur et al. ...................... 703/11
7,037,936 B2 *  5/2006  McKenna et al. ............. 514/451

OTHER PUBLICATIONS

Looney et al., Proc. Nat. Acad. Sci., 1975, vol. 72, No. 7, pp. 2662-2666.*
Looney et al., Cancer Research, 1980, vol. 40, p. 2179-2183.*
Gardner et al., Cancer Research, 2000, vol. 60, p. 1417-1425.*
Norton et al. (Cancer Treatment Reports, 1977, vol. 61, No. 7, 1307-17).*
Park et al. Clinical Cancer Research (Mar. 2000), vol. 6, pp. 847-854.*
Looney et al. (Cancer Research, 1980, 40: 2179-2183).*
Kelman et al. (Br. J. clin. Pharmac., 1982, 14, 247-256).*
Hethcote et al. (Radiation Research, 1973, 56: 150-161).*
New tools for cancer chemotherapy: computational assistance for tailoring treatments, Molecular Cancer Therapeutics, Jan. 1, 2003, pp. 1079-1084, vol. 2, Publisher: American Associaton for Cancer Research, (Gardener et al.).
L. Norton, Theoretical Concepts and the Emerging Role of Taxanes in Adjuvant Therapy, The Oncologist, Jun. 1, 2001, pp. 30-35, vol. 6, No. suppl 3.
R. S. Tuma, Dosing Study Seen as Victory for Clinical Trials, Mathematical Models, Journal of the National Cancer Institute, Feb. 19, 2003, pp. 254-255, vol. 95, No. 4, Publisher: Oxford University Press.

* cited by examiner

*Primary Examiner* — Lori A Clow
(74) *Attorney, Agent, or Firm* — Evans & Molinelli PLLC; Eugene J. Molinelli

(57) ABSTRACT

Techniques for determining optimal duration for treatment of disease include receiving an untreated series of measurements and a treated series of measurements. The untreated series indicates temporal progression of a physical property related to a disease while the disease is untreated. The treated series of measurements indicates temporal progression of the physical property of the disease while a particular treatment is administered. A series of effectiveness values is determined based on the untreated and treated series. Each effectiveness value indicates a ratio between an untreated and a treated rate of change of the physical property at a corresponding time. An elapsed time is determined from start of treatment to an earliest time when an effectiveness value reaches an extreme compared to adjacent effectiveness values. Duration for treatment is based on the elapsed time, and is especially useful for each cycle of dose dense regimes for treatments with toxic side effects.

17 Claims, 12 Drawing Sheets

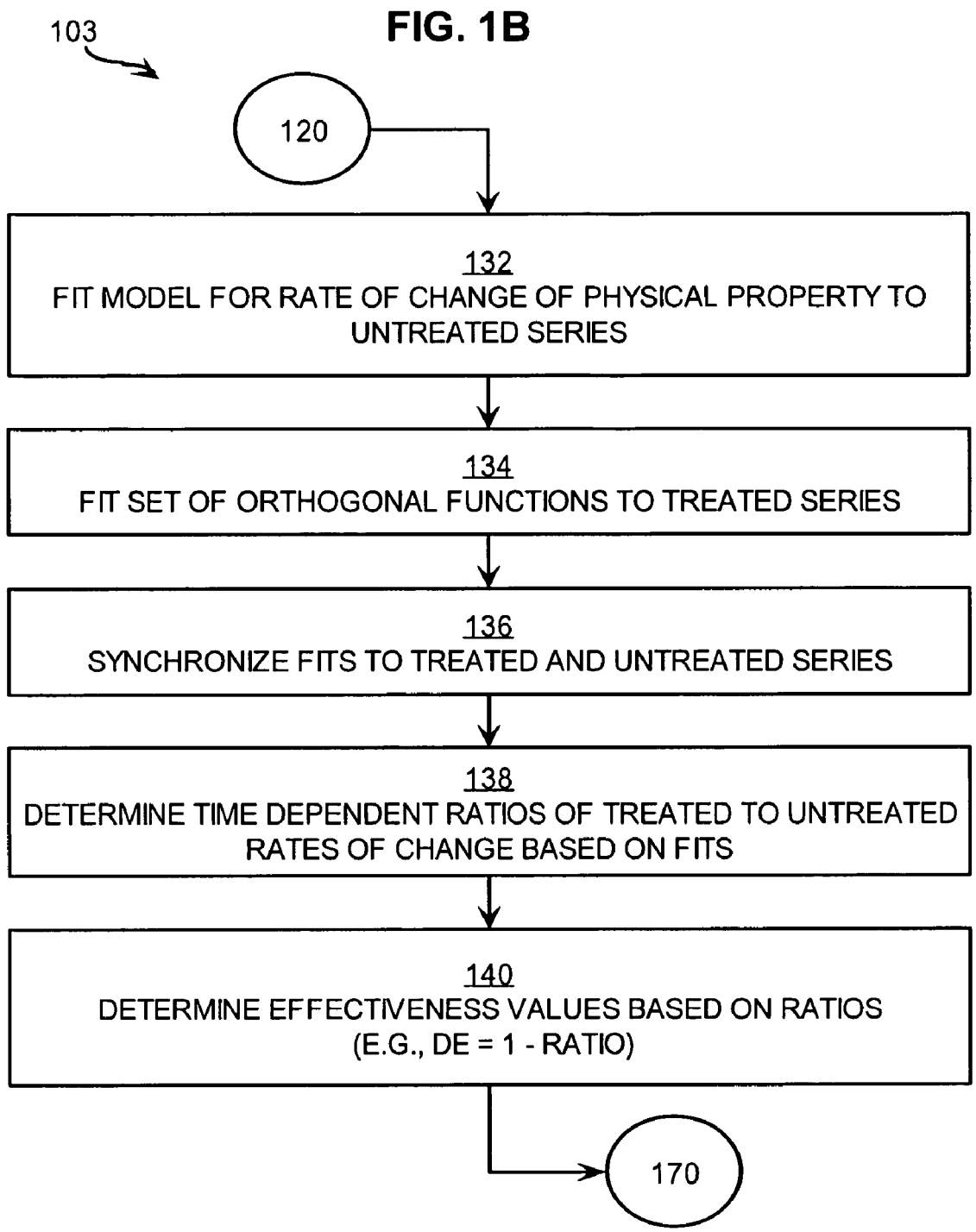

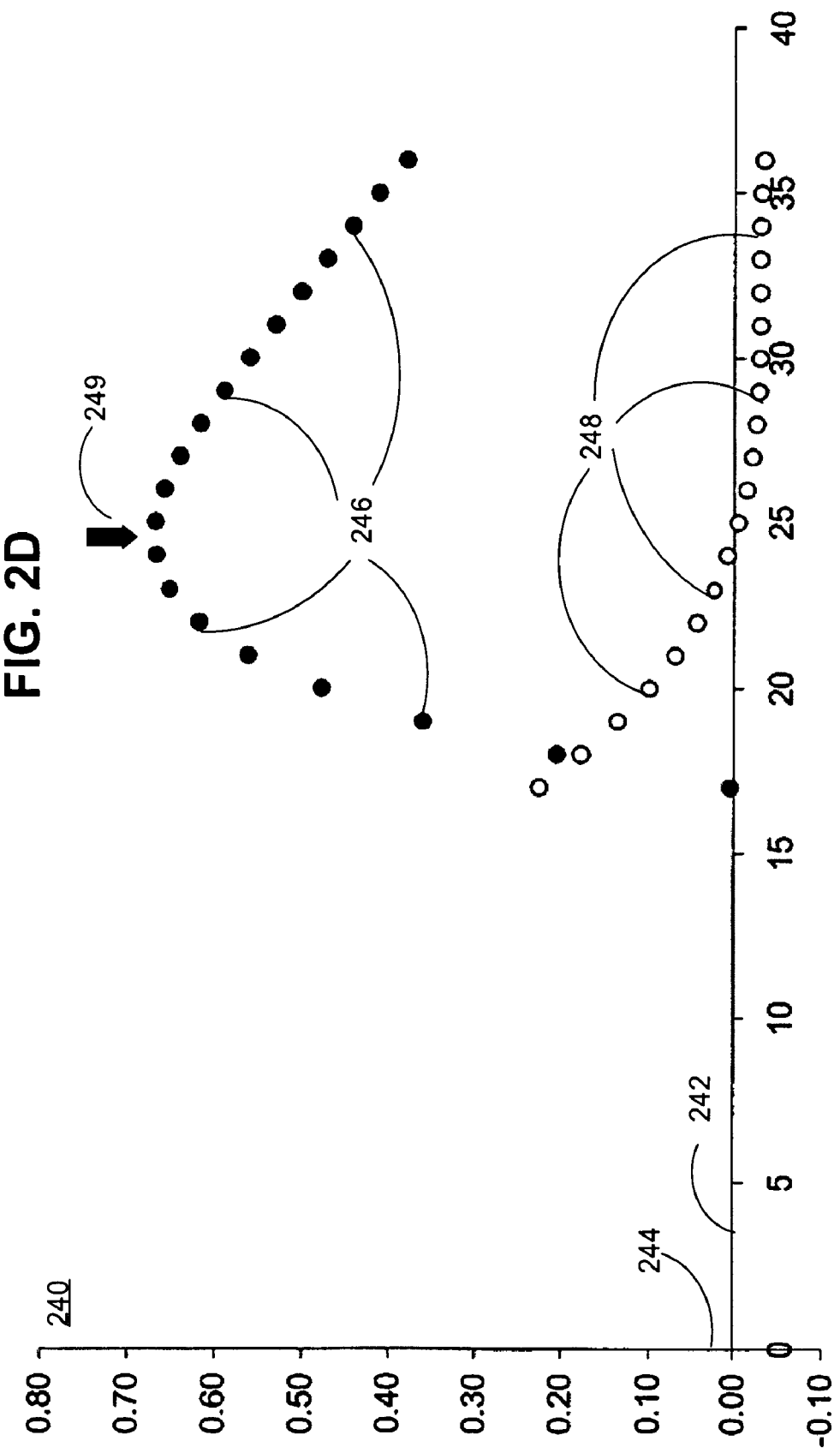

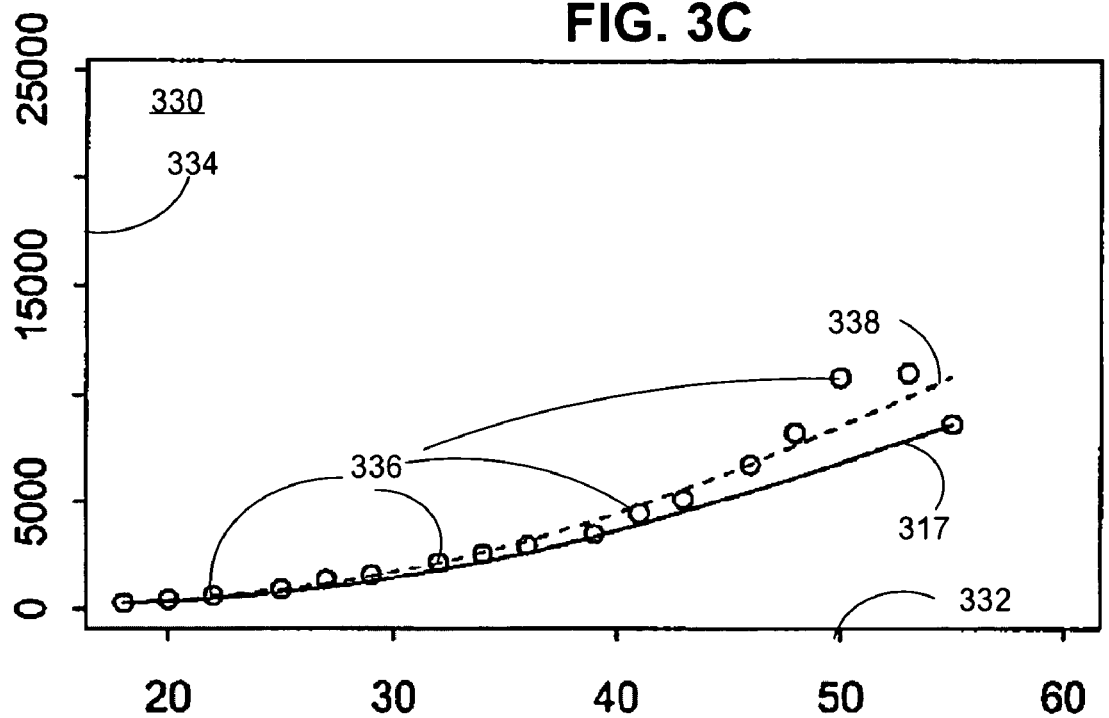
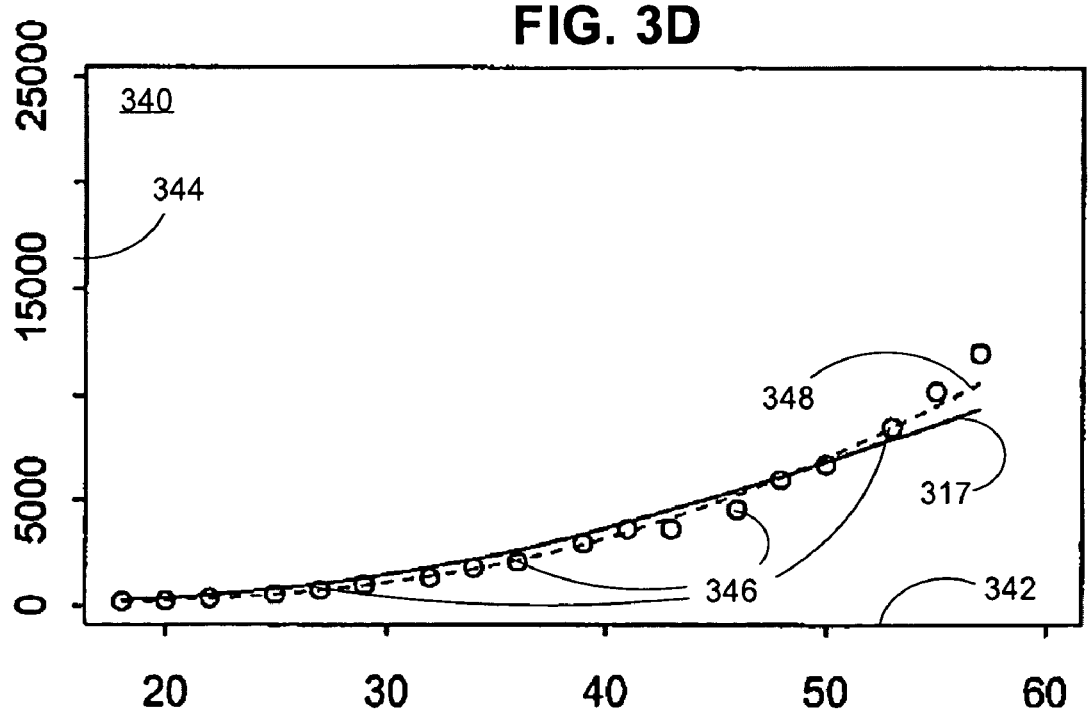

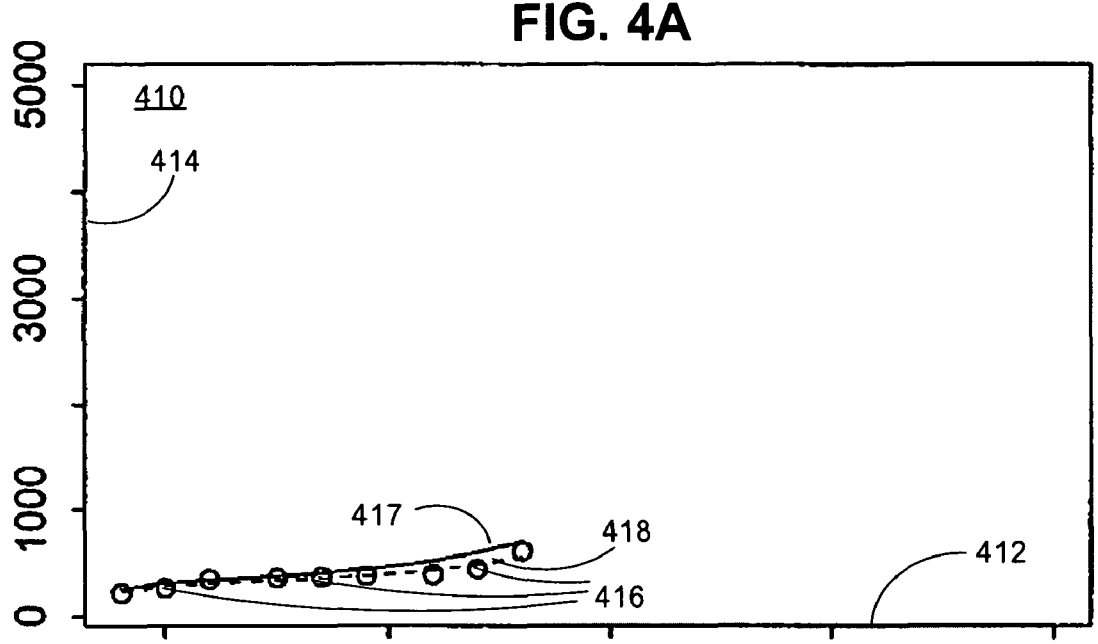
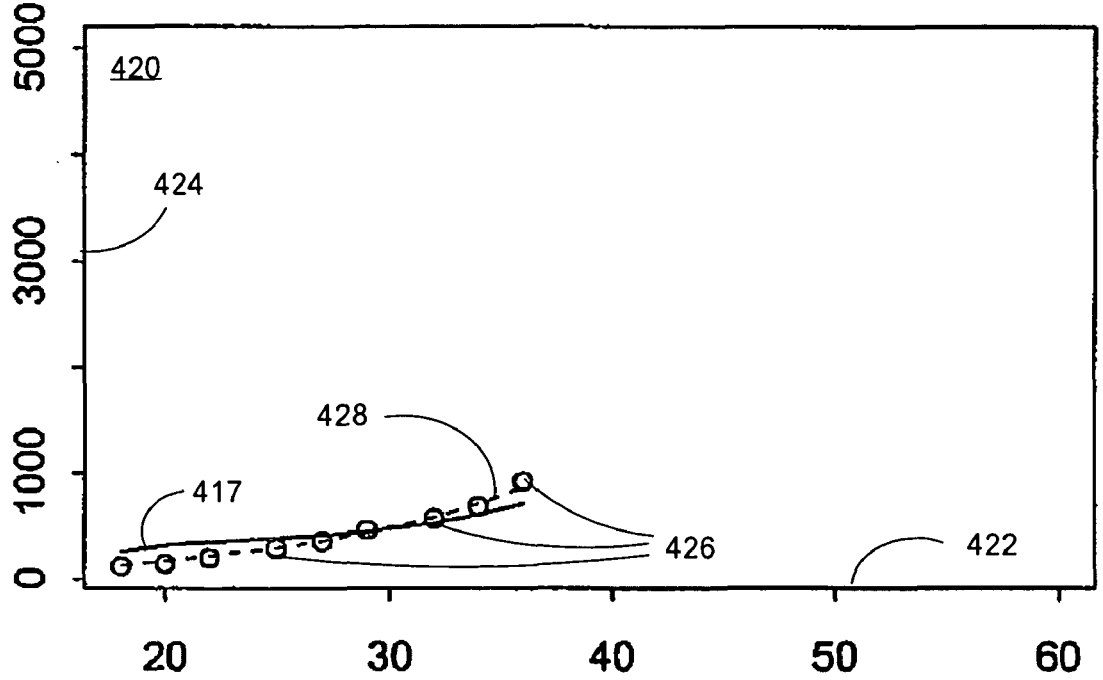

METHOD FOR DETERMINING DISEASE TREATMENT DURATION

CROSS-REFERENCE TO RELATED APPLICATIONS

This application claims benefit of Provisional Appln. 60/667,509, filed Apr. 1, 2005, the entire contents of which are hereby incorporated by reference as if fully set forth herein, under 35 U.S.C. §119(e).

This application also claims benefit of Provisional Appln. 60/672,461, filed Apr. 18, 2005, the entire contents of which are hereby incorporated by reference as if fully set forth herein, under 35 U.S.C. §119(e).

BACKGROUND OF THE INVENTION

1. Field of the Invention

The present invention relates to a method for determining treatment duration, and in particular to determining optimal treatment duration, such as for determining an optimal chemotherapeutic dose schedule [CDS], based on a time of maximum treatment effectiveness deduced from measurements.

2. Description of the Related Art

Some treatments include toxic side effects that cause harm to a patient. Effective use of such treatments requires the careful balancing of toxicity and benefit from the treatment. Many parameters influence this balance. In past approaches, effective treatment is determined by trial and error. Parameters of import are identified, such as the treatment administered (such as drug or radiation), dose of the treatment, duration of a cycle during which the treatment is administered, number of cycles, interval between the start of successive cycles (including the duration of any treatment hiatus), remedial treatment between cycles, and series of different treatments. Clinical trials are performed with a subset of all possible combinations of these factors. Clinical trials that produce the most favorable result of sufficient benefit then become an accepted protocol. However, there is rarely a determination made that any parameter of the treatment is optimal.

For example, the treatment of some cancers, including breast cancer, include the administration of one or more chemotherapeutic agents on a chemotherapeutic dose schedule (CDS) that specifies the agent, the dose of the agent, the duration of an administration cycle and an interval between the starts of successive cycles, and sometimes a number of cycles. CDS is usually determined by time-consuming, costly laboratory and clinical experiments. Optimizing CDS more efficiently than trial and error could maximize the benefit/toxicity ratio of any chemotherapeutic agent or combination of agents.

Computational models of cancer chemotherapy have the potential to streamline clinical trial design, contribute to the design of rational, tailored treatments, and facilitate our understanding of experimental results.

In one approach by L. Norton, the Gompertzian model of population growth is shown to apply to cancer cells. As a result, the Norton-Simon hypothesis was formulated which predicts that a relative advantage can be achieved if tumors are treated when they are smaller rather than larger. This leads to the conclusion that it is better to reduce the time between treatments, and thus limit the time that tumors have to increase their size. The more frequent application of chemotherapy is called a dose dense regimen for the treatment of tumors. In this regimen it is preferable to apply an effective dose of a chemotherapy agent for a shorter time so that the patient can recover more quickly and thus receive the next cycle more quickly.

Dose dense regimens have been used before, for example, in chemotherapeutic treatment of breast cancer. U.S. Patent Application 20040229826, by L. Norton, the entire contents of each of which are hereby incorporated by reference as if fully set forth herein. Norton showed that when one is administering to the patient one or more types of chemotherapeutic agent in a plurality of treatments, the results are improved by making use of the optimal amount of each type of chemotherapeutic agent and giving the treatments in a dose-dense protocol, preferably at the shortest tolerated intervals. It was shown that disease-free survival (DFS) was significantly prolonged for the dose-dense regimens compared with typical regimens that start a cycle every three weeks ("three-week regimens"). Further, overall survival (OS) was significantly prolonged in the dose-dense regimens, even after adjusting for the standard clinical pretreatment variables mentioned previously. The DFS and OS advantages of dose density were not accompanied by an increase in toxicity. Thus sequential chemotherapy that maintains dose density preserved efficacy while reducing toxicity. Sequential dose-dense single agent therapy could permit the rapid integration of new drugs into therapeutic regimens, including biological agents.

The selection of a value for duration of administration of treatment on each cycle is an important step in the application of the dose dense treatment. Trial and error methods, such as were used in past studies, to select the cycle duration are themselves time consuming and expensive. Computational models have the potential to speed the determination of the duration for a treatment cycle.

Based on the preceding discussion, there is a clear need for a method to determine a more optimal duration of treatment administration for each cycle of treatment, without a large number of clinical trials. In particular there is a need for application of a computational model to interpret measurements to determine the duration of a treatment cycle.

SUMMARY OF THE INVENTION

Computational models of cancer chemotherapy have the potential to streamline clinical trial design, contribute to the design of rational, tailored treatments, and facilitate our understanding of experimental results. According to some embodiments of the invention, a computation model is used to interpret measurements to determine an optimal duration for treatment administration during a treatment cycle.

In one set of embodiments, a method for determining optimal duration for treatment of disease includes receiving an untreated series of measurements and a treated series of measurements. The untreated series indicates temporal progression of a physical property related to a disease while the disease is untreated. The treated series of measurements indicates temporal progression of the physical property of the disease while a particular treatment is administered. A series of effectiveness values is determined based on the untreated and treated series. Each effectiveness value indicates a ratio between an untreated and a treated rate of change of the physical property at a corresponding time. An elapsed time is determined from start of treatment to an earliest time when an effectiveness value reaches an extreme compared to adjacent effectiveness values. Duration for treatment is based on the elapsed time, and is especially useful for each cycle of dose dense regimes for treatments with toxic side effects.

In another set of embodiments, a method for treating a patient with a disease includes receiving an untreated series of measurements and a treated series of measurements. The untreated series of measurements indicates temporal progression of a physical property related to a disease while the disease is untreated in a victim outside a population of patients to be treated. The treated series of measurements indicates temporal progression of the physical property of the disease while a particular treatment is administered, wherein the treated series includes an initial treatment measurement substantively when the treatment is started. A series of effectiveness values is determined based on the untreated series and the treated series. Each effectiveness value indicates a ratio between an untreated rate of change of the physical property while the disease is untreated at one time and a treated rate of change of the physical property while the disease is treated with the particular treatment at a corresponding time. An elapsed time is determined from start of treatment to an earliest time when an effectiveness value reaches an extreme compared to adjacent effectiveness values. A duration for administering the treatment to a particular patient with the disease is determined based on the elapsed time. The treatment is administered to the particular patient for a time that does not exceed the duration during a temporal cycle of treatment and hiatus.

In another set of embodiments, a method includes administering a treatment for a duration computed according to one or more steps of the above methods.

In other sets of the embodiment, a computer-readable medium carries instructions that cause a processor to execute one or more steps of the above methods.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1B is a flow diagram that illustrates in more detail a method for determining effectiveness values from a series of measurements for the treated and untreated disease; according to an embodiment.

FIG. 2D is a graph that illustrates effectiveness values and time derivative of effectiveness values for pooled measurements for breast cancer treated with capecitabine at a higher dose of two doses, according to an embodiment;

FIG. 3A, FIG. 3B, FIG. 3C, FIG. 3D are four graphs that illustrate measurements of tumor volume growth for untreated breast cancer in xenograft models (MX-1) for four individual animals, respectively, each fit to a model according to an embodiment and compared to a fit to the pooled measurements; and FIG. 4A, FIG. 4B, FIG. 4C, FIG. 4D are four graphs that illustrate measurements of tumor volume growth for treated breast cancer in xenograft models (MX-1) for four individual animals, respectively, each fit to polynomials according to an embodiment and compared to a fit to the pooled measurements;

DETAILED DESCRIPTION

Techniques are described for treating a patient with a disease. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Particular embodiments of the invention are descried below in the context of treating breast cancer with XELODA™, available from Hoffmann-La Roche Inc. of Nutley, N.J., US. However, the invention is not limited to this context. In other embodiments, the same or other diseases are treated with the same or different drug or non-drug treatments. For example, in some embodiments, the same type of cancer is treated with a different chemotherapy agent. In some embodiments, the same or different type of cancer is treated with radiation instead of a chemotherapy agent. In some embodiments, the disease is hypertension and the treatment is a hypertension-mitigating agent. In some embodiments, the disease is a particular dermatological condition and the treatment is a mitigating agent for the particular dermatological condition. In some embodiments the disease is osteoporosis and the treatment is alendronate sodium which is an amino-bisphosphonate marketed as FOSAMAX™ by Merck & Co., Inc. of Whitehouse Station, N.J. It is anticipated that the techniques described herein may be employed in the treatment of any disease in which there is toxicity or other cost limit on the amount and duration of the treatment administered.

1. Method and Example Embodiment

Figure 1A:
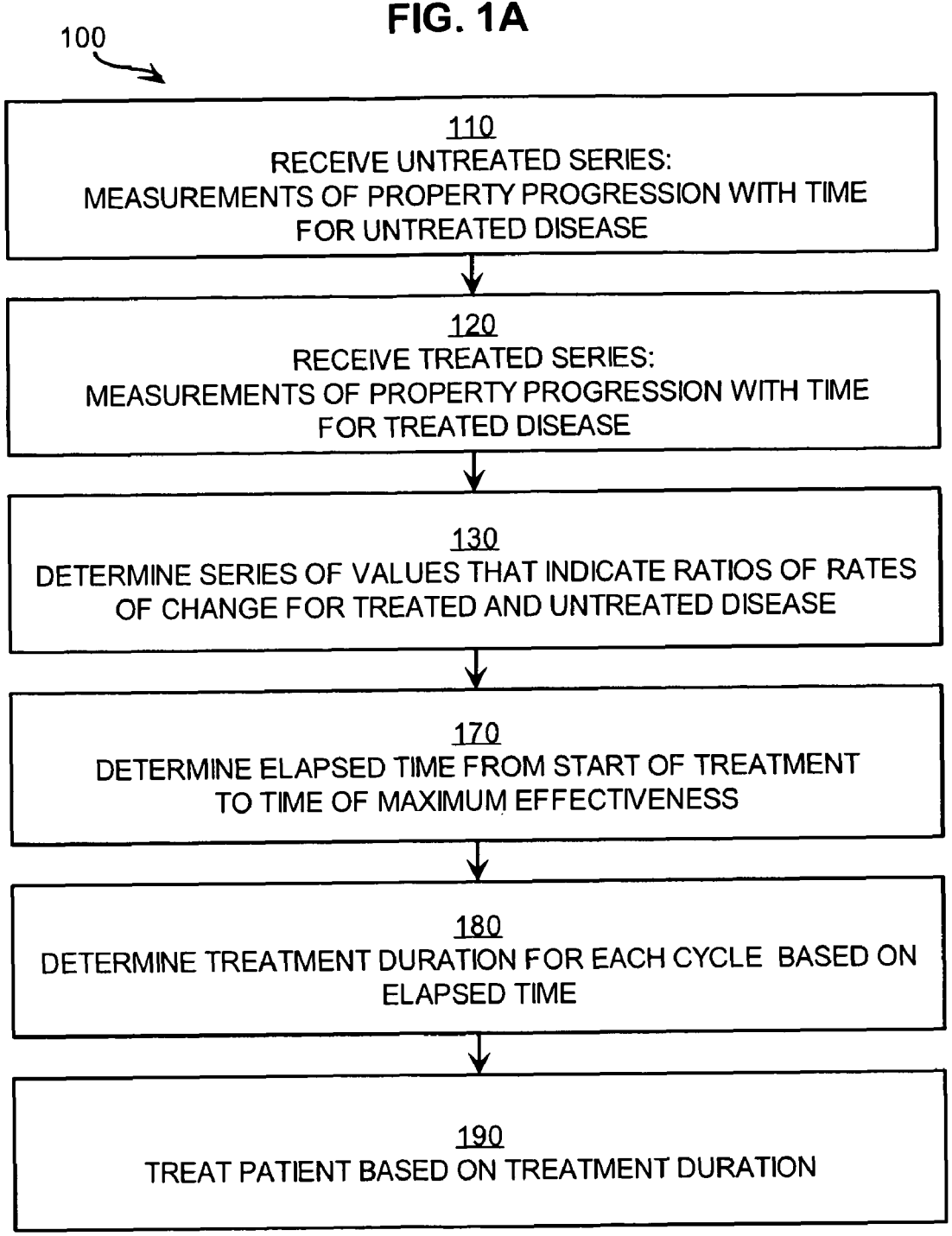
FIG. 1A is a flow diagram that illustrates at a high level a method for treating a patient suffering from a disease based on measures of treatment effectiveness, according to an embodiment.

FIG. 1A is a flow diagram that illustrates at a high level a method 100 for treating a patient suffering from a disease based on measures of treatment effectiveness, according to an embodiment. Although steps are shown in FIG. 1A and FIG. 1B in a particular order for purposes of illustrating particular embodiments, in other embodiments one or more steps may be performed in a different order, or overlapping in time, or one or more steps may be omitted, or some combination of changes may be applied.

In step 110, a series of measurements is received that reveal the temporal progression of a physical property of tissue related to a disease, when the disease is untreated. This series of measurements is called an "untreated series of measurements" herein, for convenience; but it is understood that the disease is untreated, not the measurements or their series.

Any method may be used to receive the series of measurements. For example, in some embodiments, the measurements are obtained directly from a sensor, such as from an imaging sensor. In various other embodiments, the measurements are input manually or scanned in from a paper listing or graph. In some embodiments, the measurements are received as data read from a local storage device or transmitted from a remote device over a network.

Figure 2A:
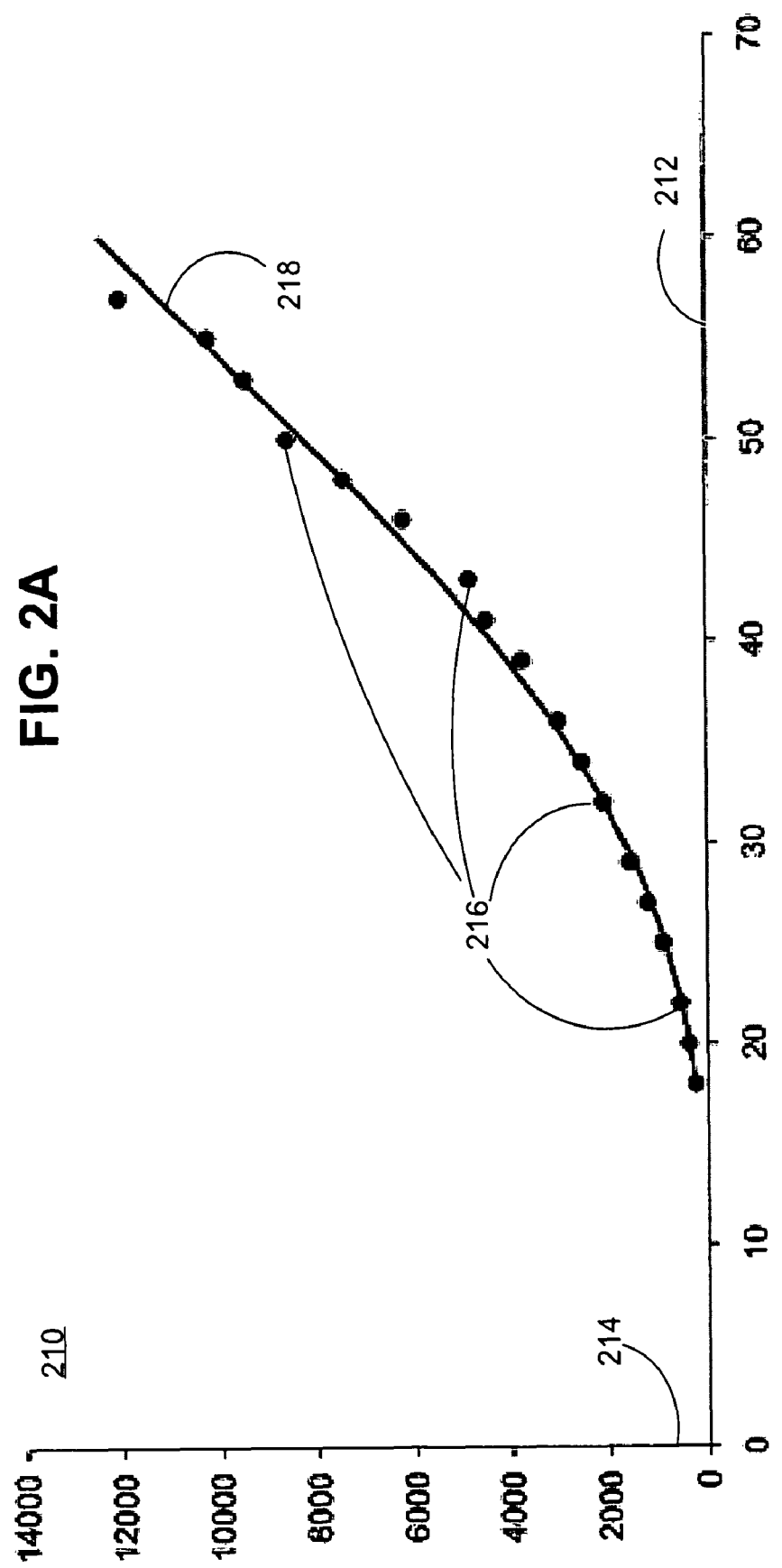
FIG. 2A is a graph that illustrates pooled measurements of tumor volume growth for untreated breast cancer in xenograft models (MX-1), fit to a model according to an embodiment.

The untreated series of measurements reveal the progression of the disease without treatment, and therefore it is not obtained from a patient to be treated using the method. Typically the untreated series of measurements describes the progression of the disease in one or more historical cases, or test subjects, or both. For example, the untreated series of measurements describes the progression of tumor volume with time in breast cancer victims who are not treated for some number of weeks. In the illustrated embodiment, described further in later sections, the untreated series of measurements describe tumor volume in mice bearing MX-1 or MAXF401 human breast cancer xenografts approximately every two days for about seven weeks (50 days). FIG. 2A is a graph 210 that illustrates, as solid-filled circles 216, pooled measurements of tumor volume growth for untreated breast cancer in xenograft models (MX-1). Untreated tumor growth is sometimes called "naïve growth." The horizontal axis 212 indicates the passage of time in days since an initial time. The vertical axis 214 indicates the tumor volume in cubic millimeters ($mm^3$). The solid trace 218 represents a model fit to the data as described in more detail below.

In step 120, a series of measurements is received that reveal the temporal progression of the physical property of tissue related to the disease, when the disease is treated in a particular way. This series of measurements is called a "treated series of measurements" herein, for convenience; but it is understood that the disease is treated, not necessarily the measurements or their series. Any method may be used to receive the treated series, as described above for the untreated series.

The treated series of measurements reveals the progression of the disease with treatment, and therefore may be obtained from a patient to be treated using the method. More typically, however, the treated series of measurements describes the progression of the disease in historical cases, or test subjects, or both. For example, the treated series of measurements describes the progression of tumor volume with time in breast cancer victims who are treated for some number of weeks using an accepted protocol or during clinical trials to develop that protocol.

In the illustrated embodiment, described further in later sections, two treated series of measurements describe tumor volume in mice bearing MX-1 or MAXF401 human breast cancer xenografts approximately every two days for about seven weeks (50 days) during treatment. The treatment involves administering the drug XELODA according to the standard protocol: a 14-day duration of administering the drug at a particular dose, followed by a 7 day hiatus in administering the drug. One treatment uses a lower dose of 1.5 millimoles (mmol) per kilogram (kg) of victim weight per day (mmol/kg/day). A second treatment uses a higher dose of 2.25 mmol/kg/day. Each of the two treated series describes the progression of tumor volume with time in the treated victim of the disease, and includes an initial measurement of tumor volume at or near when the treatment was started, for example just before the first injection of the drug. The initial measurement is used in a later step to relate a treated series to the untreated series, which typically occur in different subjects.

Figure 2B:
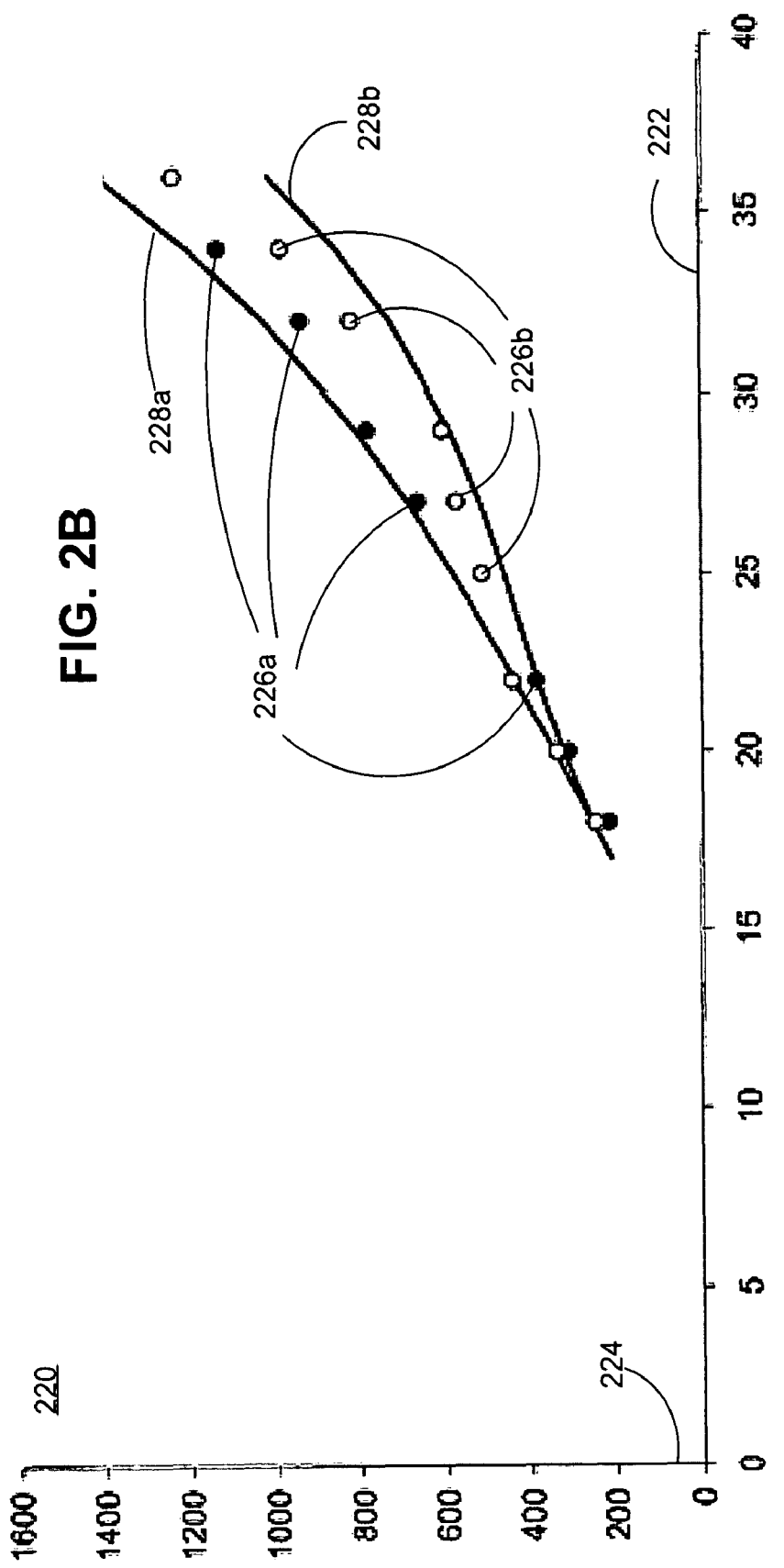
FIG. 2B is a graph that illustrates pooled measurements of tumor volume growth for breast cancer in xenograft models (MX-1) treated with capecitabine at two doses, fit with different combinations of polynomials according to some embodiments.

FIG. 2B is a graph that illustrates pooled measurements of tumor volume growth for breast cancer in xenograft models (MX-1) treated with capecitabine (XELODA) at a lower dose (solid-filled circles 226a) and a higher dose (open circles 226b). The horizontal axis 222 indicates the passage of time in days since an initial time. The vertical axis 224 indicates the tumor volume in cubic millimeters ($mm^3$). The solid traces 228a, 228b represent model fits to the data as described in more detail below.

In step 130, a temporal series of effectiveness values is determined. Any method may be used to determine an effectiveness value. In the illustrated embodiment, each effectiveness value indicates the ratio between the rate of change of the physical property for the treated disease and the rate of change for the untreated disease at a corresponding time. For purposes of illustration, it is assumed that the temporal progression of the physical property for the untreated disease is represented by the function Pu(t) and that its rate of change is given by its first time derivative Pu'(t). Similarly, it is assumed that the temporal progression of the physical property for the treated disease is represented by the function Pt(t) and that its rate of change is given by its first time derivative Pt'(t). It is further assumed that the temporal progression of the ratio is represented by the function R(t) and is given by Equation 1

$$R(t)=Pt'(t)/Pu'(t) \qquad (1).$$

In other embodiments, a different definition of ratio is used. For example, in some embodiments the ratio given by the reciprocal of R(t) is used. In the illustrated embodiments, R is the ratio of two physical properties with the same units and is therefore dimensionless.

An effectiveness parameter is often defined that indicates the ratio R(t) but offers a more useful description of the effect of a treatment than the ratio itself. For example, in the case of a tumor volume that increases in the untreated case and that increases more slowly or decreases in size for a successful drug treatment, a more useful expression of the effectiveness of a drug treatment is given by a drug effect represented by DE(t), where DE(t) is defined by Equation 2a or 2b.

$$R(t)=(1-DE(t)) \qquad (2a)$$

$$DE(t)=1-R(t) \qquad (2b)$$

When defined in this way, the value of DE is greater than zero if the tumor growth for the treated disease is less than that of the untreated disease, and is greater than one if the tumor actually shrinks in size. In some embodiments, the effectiveness value is the same as the Ratio R(t); in some embodiments the effectiveness value is based on and indicates the Ratio R(t) but is different. For example, in the illustrated embodiment, the effectiveness value is DE(t). If R is dimensionless, DE is also dimensionless.

A series of effectiveness values is obtained by evaluating the effectiveness temporal function at discrete times, e.g., by evaluating R(t) or DE(t) at discrete times. The determination of the series of effectiveness values that indicate the ratios is described in more detail bellow with respect to FIG. 1B.

Figure 2C:
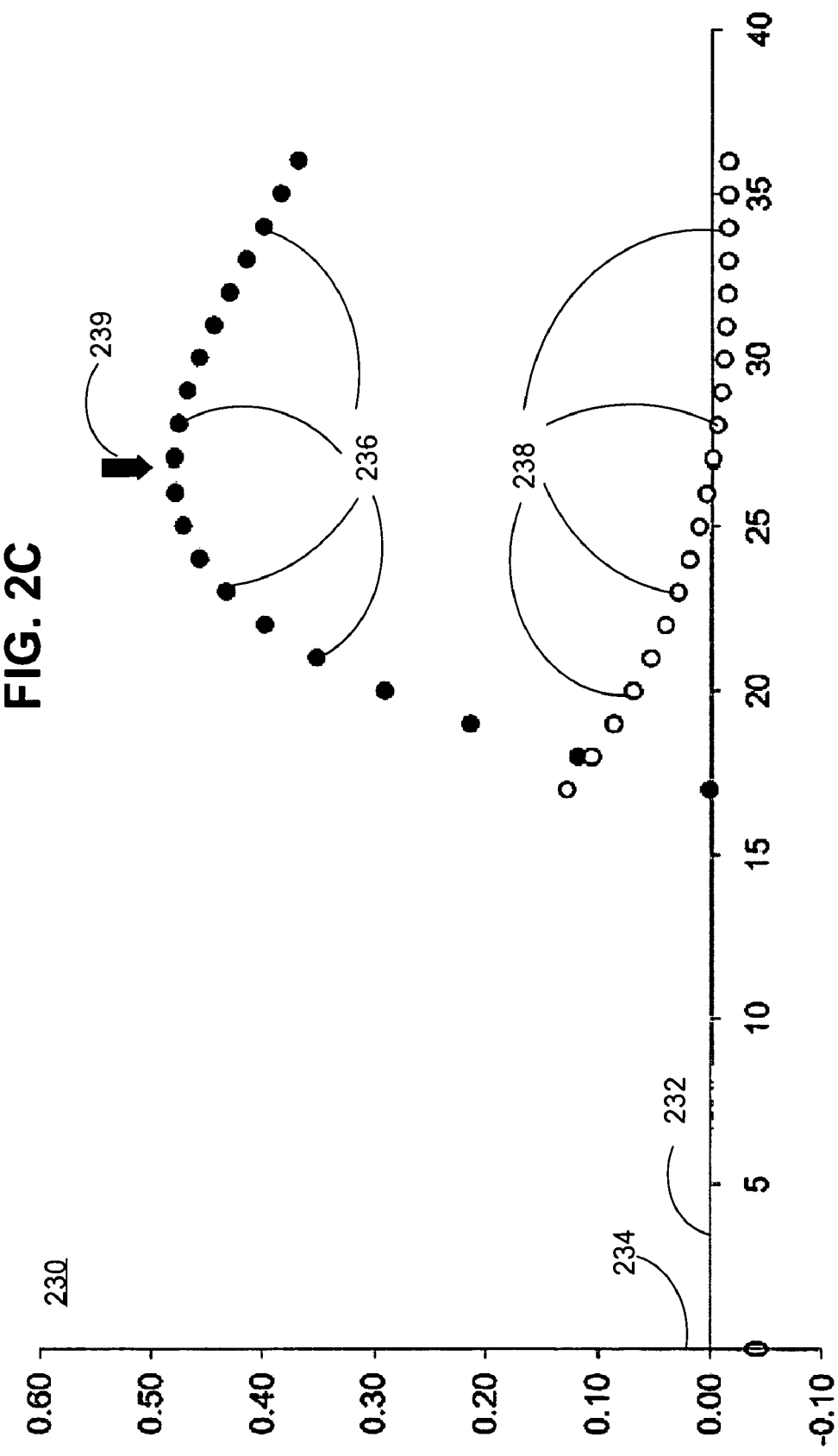
FIG. 2C is a graph that illustrates effectiveness values and time derivative of effectiveness values for pooled measurements for breast cancer treated with capecitabine at a lower dose of two doses, according to an embodiment.

FIG. 2C is a graph 230 that illustrates, as solid circles 236, DE(t) for pooled measurements for breast cancer treated with capecitabine at a lower dose of two tested doses, according to an embodiment. The horizontal axis 232 indicates the passage of time in days since an initial time. The vertical axis 234 indicates a numeric value for a variety of quantities, including dimensionless quantities. Also plotted in graph 230, as open circles 238, is the temporal rate of change of DE(t) as described in more detail below, in units of changes of DE(t) per day.

FIG. 2D is a graph 240 that illustrates, as solid circles 246, DE(t) for pooled measurements for breast cancer treated with capecitabine at a higher dose of two tested doses, according to an embodiment. The horizontal axis 242 indicates the passage of time in days since an initial time. The vertical axis 244 indicates a numeric value for a variety of quantities. Also plotted in graph 240, as open circles 248, is the temporal rate of change of DE(t) as described in more detail below, in units of change of DE(t) per day. Thus the only difference between graph 230 in FIG. 2C and graph 240 in FIG. 2D is the dose of the treatment given.

In step 170, the elapsed time after start of treatment until the effectiveness values reaches an extreme is determined.

In some circumstances, it might be expected that the effectiveness increases with increased administration of the treatment (though the toxic or other costs often also increase). In such embodiments, the extreme value is the last value of the series. However, it has been observed by the applicant that in many circumstances, including tumor growth which slows with increasing tumor size, the effectiveness increases to a maximum effectiveness as treatment endures, called the "time point of maximum impact" (TPMI) of treatment herein, after which effectiveness decreases. Continuing treatment beyond this TPMI indicates that the treatment is having less effect just as the toxic and other costs are increasing. The cost-benefit balance is expected to reverse at this point. Whether the extreme position is a maximum or minimum depends on whether the effectiveness value varies directly or inversely with the effectiveness of the treatment. For example, if the ratio R(t) is used as the effectiveness parameter for tumor growth, the cost-benefit reversal occurs at a minimum in R(t).

As is well known from principles of calculus, a relative maximum or minimum in a function is associated with a value of zero in the derivative of the function.

In step 170, the elapsed time to the extreme value indicates the TPMI. The TPMI is given by the times of the relative maximum in DE(t) for the low dose and high dose treatments, and are indicated by arrows 239 in FIG. 2C and 249 in FIG. 2D, respectively. The maximum time is day 27 (corresponding to an elapsed time 10 days after start of treatment) for the lower dose and day 25 (corresponding to an elapsed time 8 days after start of treatment) for the higher dose. The derivative of DE(t) with respect to time is represented by DE'(t) and is illustrated by open circles 238 in FIG. 2C and 248 in FIG. 2D, respectively. The derivative DE'(t) represented by open circles 238 crosses zero at day 27.1 for the lower dose; and the derivative represented by open circles 248 crosses zero at day 25.3 for the higher dose, as indicated above by the arrows 239, 249 in those figures. These zero crossings correspond to elapsed times of 10.1 and 8.3 days, respectively. Using the zero crossing of the derivative gives a more precise value for TPMI and the elapsed time.

In step 180, a treatment duration is determined based on the elapsed time to the relative extreme in effectiveness values, e.g., the relative maximum in DE(t). For example, based on the elapsed times of 8.3 days for the higher dose and 10.1 days for the lower dose, a treatment duration of 7 days is determined. The elapsed times of 8.3 and 10.1 indicate that the standard duration of 14 days is too long and likely passes the cost-benefit reversal of the treatment. A duration of 7 days is less than the TPMI, allows for a higher dose to be administered, and allows a second cycle to begin more rapidly than using the standard protocol of 14 days duration and 7 days hiatus.

Figure 2E:
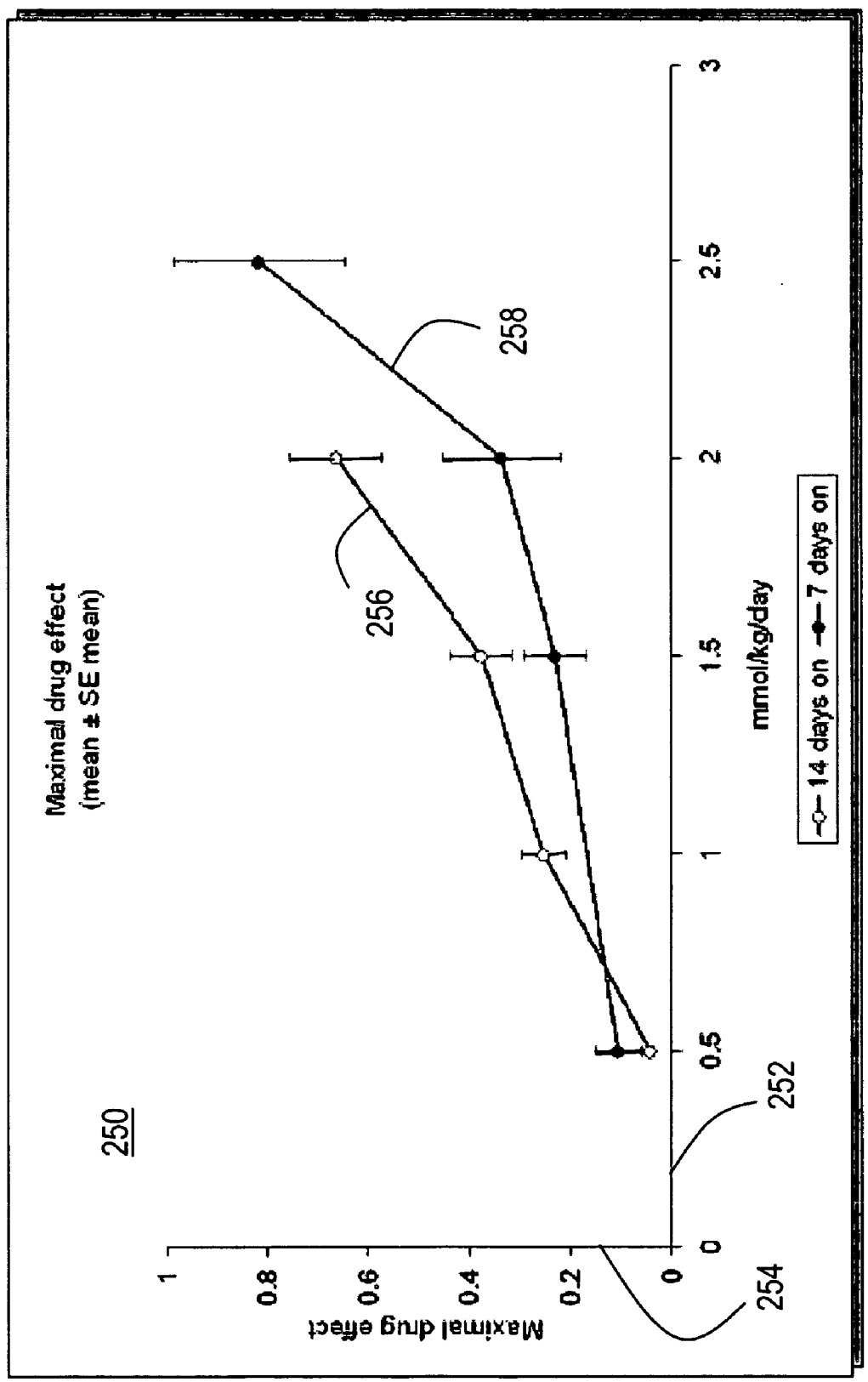
FIG. 2E is a graph that illustrates results of treatment using the shorter duration determined according to an embodiment compared with a different standard protocol using a longer duration.
Figure 3A:
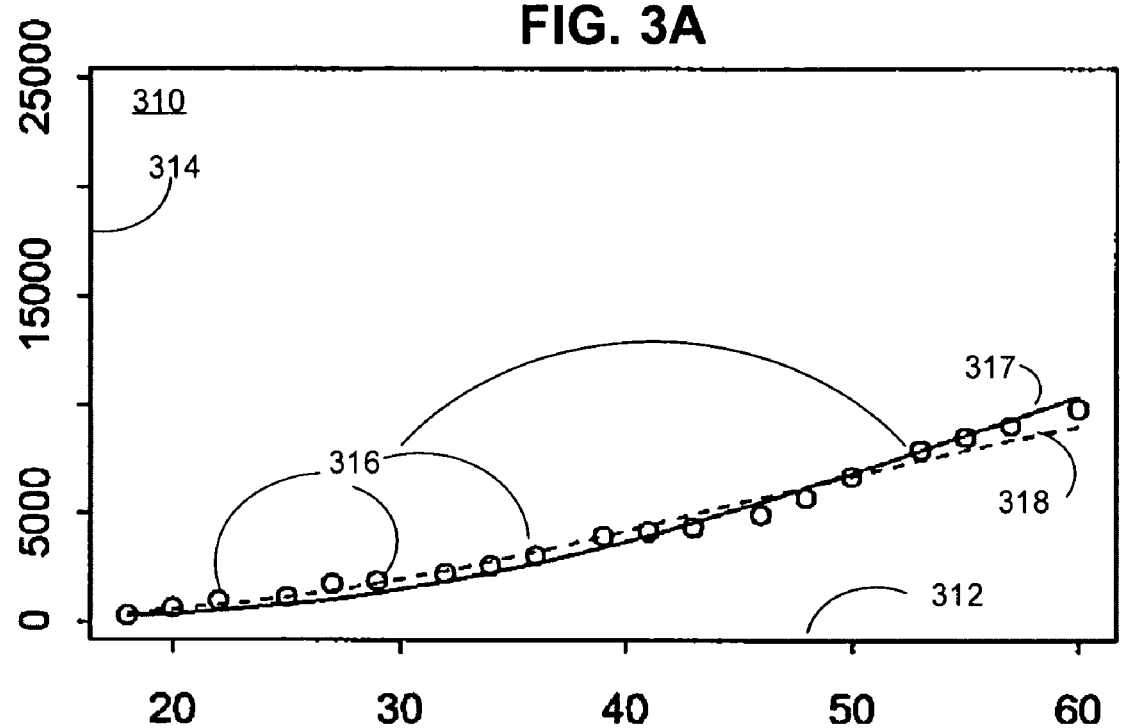
Figure 3B:
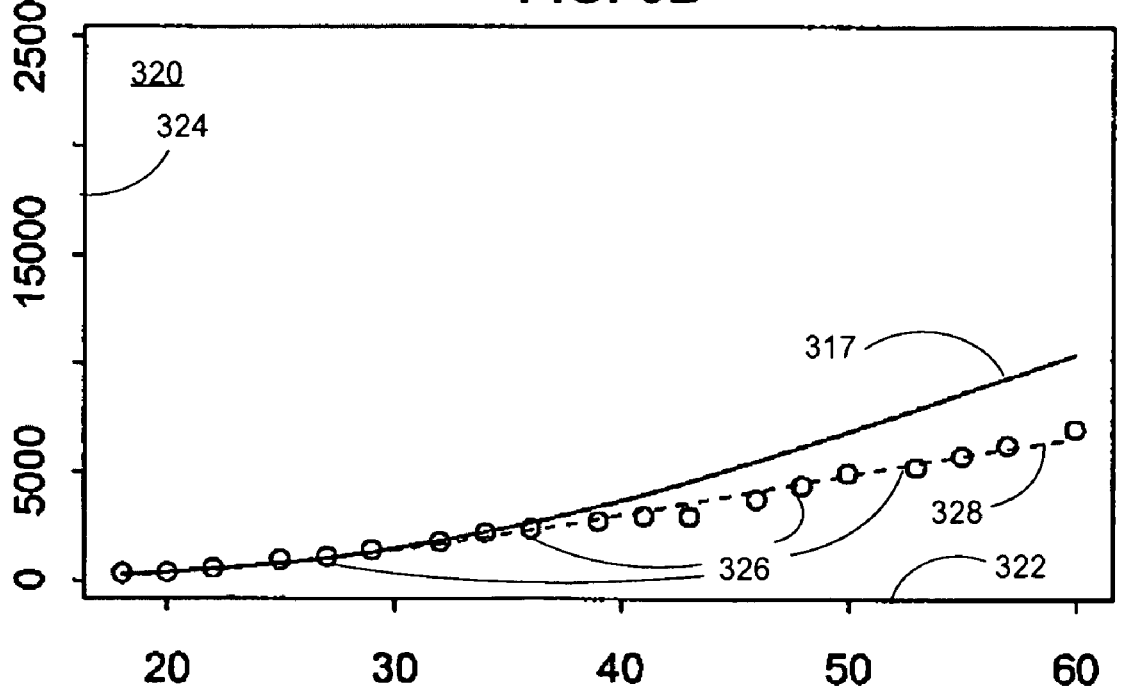
Figure 4C:
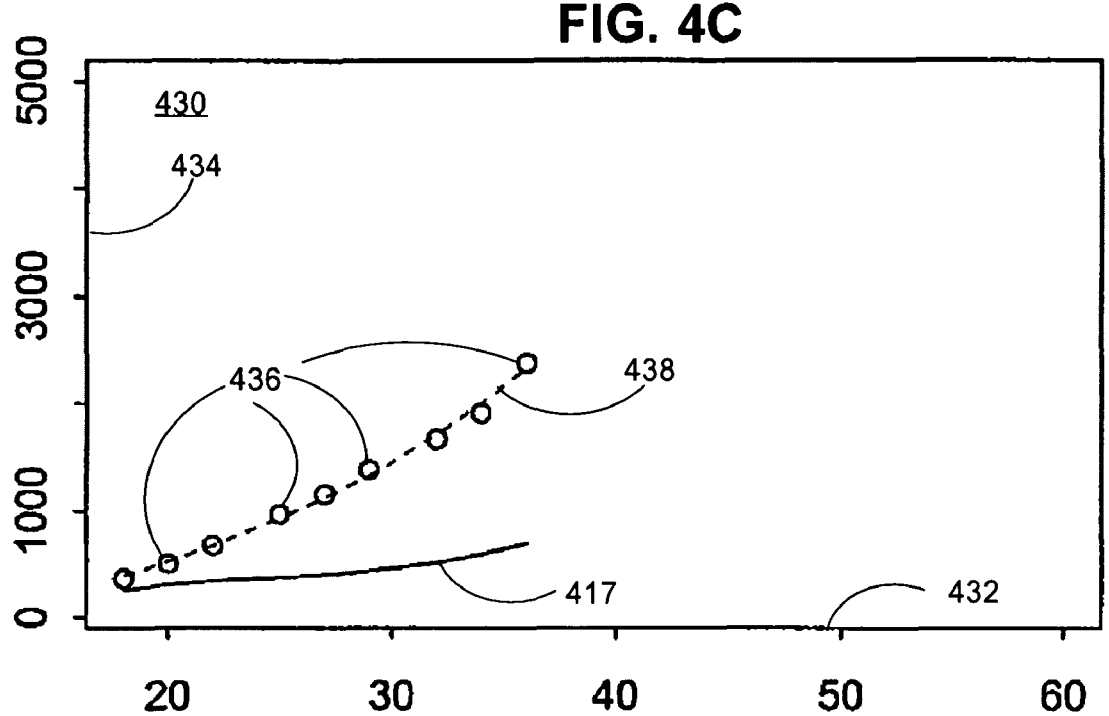
Figure 4D:
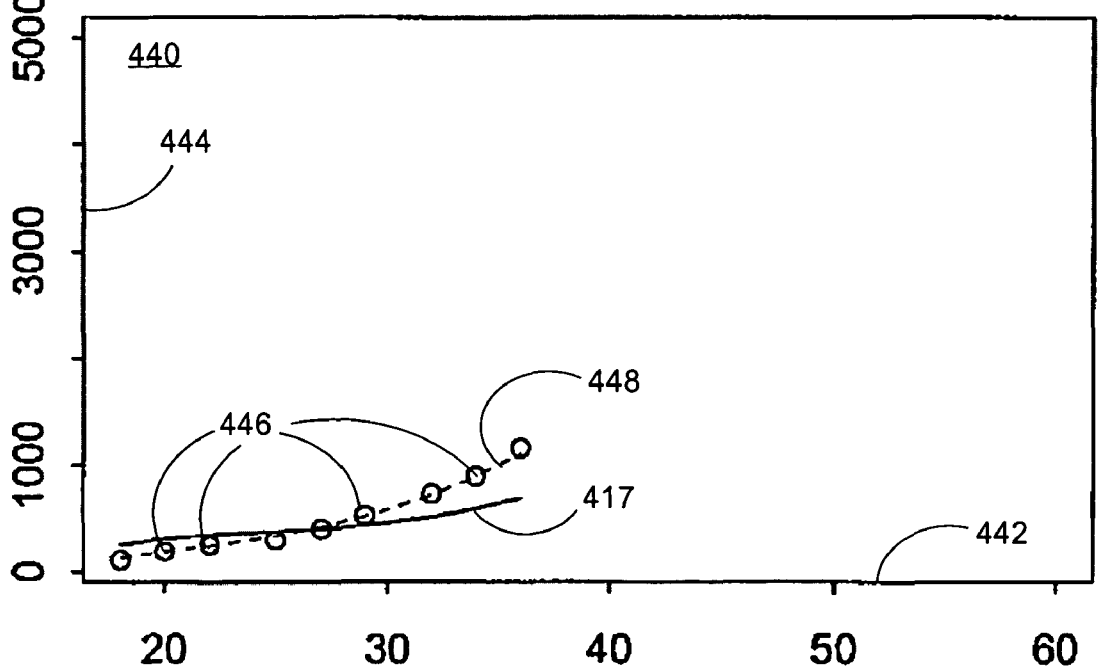

In step 190 a patient is treated based on the duration determined in step 180. For example, a patient is treated with a CDS having a 7-day duration of treatment followed by a 7-day hiatus. FIG. 2E is a graph 250 that illustrates results of treatment using the 7-day duration (solid-filled circles forming trace 258) compared to the standard protocol using a longer, 14-day duration (open circles forming trace 256). The horizontal axis 252 indicates the dosage in mmoles/kg/day. The vertical axis 254 indicates the maximum drug effect, DE(TPMI), a dimensionless quantity. The maximum drug effect, DE(TPMI), increase with dose. As shown by this graph, the shorter duration allows a higher dose (2.5 mmol/kg/day) than allowed by the standard protocol, resulting in a larger drug effect than likely achievable using the longer duration protocol (a DE of about 0.8 for the high dose compared to about 0.65 for the standard protocol).

The illustrated embodiment treats a particular patient using the duration based on pooled data from test subjects. In some embodiments, the treatment is particularized for an individual patient. For example, a particular patient with a tumor receives a certain dose of a drug each day starting on an initial day. After each day, $d_i$, the tumor size is measured and added to the treated series. The time rate of change of the tumor size and the value of DE for the present day, $DE(d_i)$ is determined in step 130. If the new value $DE(d_i)$ is less than the value of $DE(d_{i-1})$ for the previous day $d_{i-1}$, then the TPMI is determined to be day $d_{i-1}$. Then the elapsed time is determined from the initial day to day $d_{i-1}$. This value of the elapsed time is then used in step 180 to determine a treatment duration. For example, a hiatus based on the elapsed time from the initial day to day $d_{i-1}$, is started on the next day, day $d_{i+1}$.

FIG. 1B is a flow diagram that illustrates in more detail a method 103 for determining effectiveness values from series of measurements for the treated and untreated disease, according to an embodiment. Method 103 is an embodiment of step 130, and thus receives control from step 120 and passes control to step 170 in the illustrated embodiment.

The series of measurements are made up of discrete values at different times and can not be expected to be temporally aligned for computing the ratio R(t) directly from the measurements at any arbitrary time t. For purposes of illustration, it is assumed that the untreated values are available at times ri, i=1, N; and that the treated values are available at times sj, j=1, M. Some interpolation in time is performed to generate Pu(t) from the untreated series Pu(ri) and to generate Pt(t) from the treated series Pt(sj). In addition, the temporal resolution of the interpolated values for R(t) and DE(t) are limited by the temporal resolution of the series of measurements, e.g., by the temporal separations among the ri and the temporal separations among the sj. For purposes of illustration, it is assumed that outputs are desired for the series of effectiveness values at arbitrary times midway between measurements of the treated disease, e.g., at times midway between sj, j=1, M.

Human cancers in general, and breast cancers in particular, usually grow by non-exponential Gompertzian kinetics, as described by L. Norton, in "A Gompertzian model of human breast cancer growth," *Cancer Res.*, vol 48, pp 7067-7071, 1977, and L. Norton, R. Simon, J. D. Brereton and A. E. Bogden, "Predicting the course of Gompertzian growth," *Nature*, vol. 264, pp 543-545, 1976, the entire contents of each of which are hereby incorporated by reference as if fully set forth herein. Therefore the untreated series can be both interpolated and extrapolated using the Gompertzian model of tumor growth, given by Equation 3.

$$dTV/dt = a*TV - ((a/\log(TVinf)*TV*\log(TV)) \qquad (3)$$

where TV is tumor volume, a and TVinf are parameters used to fit the model to data for a particular type of tumor and dVT/dt represents the time derivative of the tumor volume TV, i.e., the rate of change of the tumor volume TV.

In other embodiments, other physical properties that change according to known models use those known models to determine values of the untreated properties at an arbitrary time. In still other embodiments, physical properties for which models of change rates are unknown can still be interpolated using known functions or linear combinations of orthogonal functions such as polynomials and Fourier components.

In step 132, a model is fit to the rate of change of the physical property for the untreated series. In the illustrated embodiment, the Gompertzian model, Equation 3, is fit to the untreated series Pu(ri), i=1, N. Any model fitting approach may be used. The model fit was performed with non-linear mixed effects population modeling using software available from the NONMEM Project at the University of California at San Francisco. This fit results in particular values for a and TVinf that lead to a good match for the pooled data for the untreated series, as shown by the solid line in FIG. 2A and in FIG. 3A, FIG. 3B, FIG. 3C, and FIG. 3D.

FIG. 3A, FIG. 3B, FIG. 3C, FIG. 3D are four graphs 310, 320, 330, 340, respectively, that illustrate measurements of tumor volume growth for untreated breast cancer in xenograft models (MX-1) for four individual animals, respectively, each fit to the Gompertzian model according to an embodiment and compared to a fit to the pooled measurements. In each graph 310, 320, 330, 340 the horizontal axis, 312, 322, 332, 342, respectively, indicates the passage of time in days since an initial time. In each graph 310, 320, 330, 340 the vertical axis 314, 324, 334, 344, respectively, indicates the tumor volume in $mm^3$. The solid trace 317 represents the Gompertzian model fit to the pooled data as shown by trace 218 in FIG. 2A. The dashed traces 318, 328, 338, 348 in graphs 310, 320, 330, 340, respectively, represent Gompertzian model fits to the data for the four individual animals.

Individual fits provide different values of a and TVinf for each animal, and lead to the good matches to data illustrated by the dashed lines 318, 328, 338, 348 compared to the observations 316, 326, 336, 346, respectively. Using these fits, the rate of change of the physical property for the untreated disease, Pu'(t), can be determined at an arbitrary time t, either for the pooled data or for individual animals.

In step 134, a smooth function is fit to the physical property for the treated series, so that a rate of change can be determined that is not dominated by noise. In the illustrated embodiment, a linear combination of polynomial functions is fit to the treated series Pt(sj), j=1, M. Any model fitting approach may be used. This fitting step results in particular values for polynomial parameters that lead to a good match for pooled data of treated series, for each dose, as shown by the solid lines 228a, 228b in FIG. 2B and in FIG. 4A, FIG. 4B, FIG. 4C, and FIG. 4D.

FIG. 4A, FIG. 4B, FIG. 4C, FIG. 4D are four graphs that illustrate measurements of tumor volume growth for treated breast cancer in xenograft models (MX-1) for four individual animals, respectively, each fit to polynomials according to an embodiment and compared to a fit to the pooled measurements. In each graph 410, 420, 430, 440 the horizontal axis, 412, 422, 432, 442, respectively, indicates the passage of time in days since an initial time. In each graph 410, 420, 430, 440 the vertical axis 414, 424, 434, 444, respectively, indicates the tumor volume in $mm^3$. The solid trace 417 represents a polynomial fit to the pooled data as shown by trace 228a in FIG. 2B. The dashed traces 418, 428, 438, 448 in graphs 410, 420, 430, 440, respectively, represent polynomial fits to the data for the four individual animals.

Individual fits provide different values of polynomial parameters for each animal, and lead to the good matches to data illustrated by the dashed lines 418, 428, 438, 448 compared to the observations 416, 426, 436, 446, respectively.

These fits give the physical property for the treated disease Pt(t) at an arbitrary time t for either the pooled data or for the data of individual animals. Taking the time derivative of this polynomial combination gives the rate of change of the physical property for the treated disease Pt'(t) at an arbitrary time t.

In step 136, the fits to the treated and untreated series are synchronized so that corresponding times in the two fits can be determined. A time is determined when the fit based on the untreated series indicates a value of the physical property that is substantively equal to a value of the physical property at the initial treatment measurement. This time is set equal to the time that treatment is initialized.

For example, the Gompertzian model indicates that the tumor volume is 200 cubic millimeters ($mm^3$) on day 17, and the treated series of measurements indicates the tumor volume is 200 $mm^3$ on the first day of treatment. Therefore, the first day of treatment is taken to be day 17 of the tumor, and the two fits for the treated and untreated series are synchronized.

In step 138, the time-dependent ratio R(t) is determined based on the fits to the treated and untreated series using Equation 1.

In step 140, the time-dependent effectiveness parameter is determined based on the time-dependent ratio R(t). For example, DE(t) is determined using equation 2b. In an illustrated embodiment using a Gompertzian model for untreated tumor growth, step 138 is omitted and DE is determined directly from the synchronized fits to the treated and untreated series, as shown in Equation 4.

$$DE(t)=1-R(t) \tag{4a}$$

$$DE(t)=1-Pt'(t)/Pu'(t) \tag{4b}$$

$$DE(t)=1-Pt'(t)/[a*TV-((a/\log(TVinf)*TV*\log(TV)] \tag{4c}$$

In illustrated embodiments, the values of DE(t) are computed for pooled data and for individual animals. Daily values for DE(t) are shown for the pooled data in FIG. 2C for the lower dose and FIG. 2D for the higher dose. Values for DE(t) are also computed but not shown for individual treated animals (e.g., animals 11 through 30) for both one cycle and two cycles.

2. Further Detailed Embodiments

Additional detailed embodiments are described in this section. Section 2.1 describes an illustrated embodiment using pooled data from 30 mice. Section 2.2 describes example embodiments using individual mice. In both these embodiments, method 100 is used to determine dosage duration for XELODA™ (X). XELODA is an oral tumor-activated fluoropyrimidine carbamate active against metastatic breast and colorectal carcinoma, now used alone or in combination twice daily for 14 consecutive days every 3 weeks.

These embodiments show that administration of capecitabine in 7 on/7 off CDS, as determined by the method 100, rather than 14 on/7 off CDS approved by the US Food and Drug Administration (FDA), allows for: 1] higher daily dosage (dose dense); 2] increased efficacy; and 3] optimized clinical benefit.

2.1 Pooled Mice

Mice bearing MX-1 or MAXF401 human breast cancer xenografts received 6 weeks of X on one of 4 chemotherapeutic dose schedule (CDS) regimens (days on/off): 14/7, 5/2, 2/5, 7/7. Each CDS evaluated 4 dose levels plus control, and all were effective at an appropriate dose (Yanagisawa, Proc. AACR #3086, 2004, hereinafter Yanagisawa). The data were analyzed for the approved (14/7) CDS by measuring at each time point after the initiation of therapy the ratio of the (data-derived) expected Gompertzian growth rate in the unperturbed (control) state compared with that observed in the treated state. Curve-fitting was by non-linear mixed-effect population modeling using NONMEM software.

The time point of maximum impact (TPMI) of treatment is when the absolute value of the ratio of growth rates (perturbed/control) is greatest as determined by methods of calculus, e.g., where the derivative crosses zero, as described above. For all dose levels analyzed this point averaged from 8.3-10.1 days into therapy, with the impact of treatment decreasing thereafter despite administration for 14 days. Schedules shorter than 14 days in length can deliver higher dose levels safely. Hence administering one week of treatment as often as clinically feasible (dose density) is expected to provide optimal benefit vs. toxicity. As illustrated by this embodiment, mathematical modeling using the Norton/Simon model predicts maximal drug effect, thereby determining CDS for optimal efficacy to toxicity for capecitabine (X).

Yanagisawa compared different schedules of capecitabine and used four dose levels (+control) adjusted to the same total dosage over 6 weeks. This did not allow comparison of the different treatment schedules with each other in terms of dosage, toxicity, and efficacy. The current embodiment includes a new series of experiments designed to explore different schedules at four dose levels (+control) but also allowed for comparisons among different treatment schedules. The same daily dosages were given in each of the schedules for each dose level. Unlike Yanagisawa, this led to different total dosages over a 6-week treatment period.

The Gompertzian growth model was applied to naïve tumor growth data for the standard schedule of capecitabine (14 days on/7 day off) in animal model of breast cancer. The standard 14/7 CDS was chosen because it is FDA approved and 14 days of ongoing treatment allows sustained observation of drug effect measured as reduction of tumor volume or tumor volume growth.

The drug effect (DE) as defined above was estimated for 1.5 and 2.25 mmol/kg/day groups during first cycle of treatment. The duration when drug effect is maximal (e.g., TPMI) was determined as described above. Data were analyzed using a non-linear mixed effects population modeling approach with the NONMEM software. The TPMI of treatment indicates when the absolute value of the ratio of growth rates (perturbed/control) is greatest. For the two dose levels analyzed, this point averaged from 8.3-10.1 days into therapy, as shown in FIG. 2C and FIG. 2D by arrows 239, 249, respectively. The impact of drug effect (DE) decreases after TPMI despite continued therapy.

A follow-up experiment compared 7 days on and 7 days off therapy with "standard" dosing. 7 on/7 off CDS allowed delivery of a higher daily dose yielding increased maximal DE compared with 14 on/7 off CDS, as shown in FIG. 2E.

2.2 Individual Mice

Using treated series for individual mice, the TPMI for the lower dose was found to vary from about 6 to about 11 days; and the TPMI for the higher dose was found to vary from about 5 to about 18 days. Example tumor growth for 4 untreated mice are shown in FIGS. 3A through 3D, along with Gompertzian models fit to the data for each mouse and the Gompertzian model fit for the pool of all untreated mice. Example tumor growth through the first cycle of treatment for 4 treated mice are shown in FIGS. 4A through 4D, along with a polynomial fit to the data for each mouse and a polynomial fit for the pool of all treated mice. These values of DE for individual animals thus supports a more general use of shorter duration, higher dose CDS regimens.

3. Hardware Overview

Figure 5:
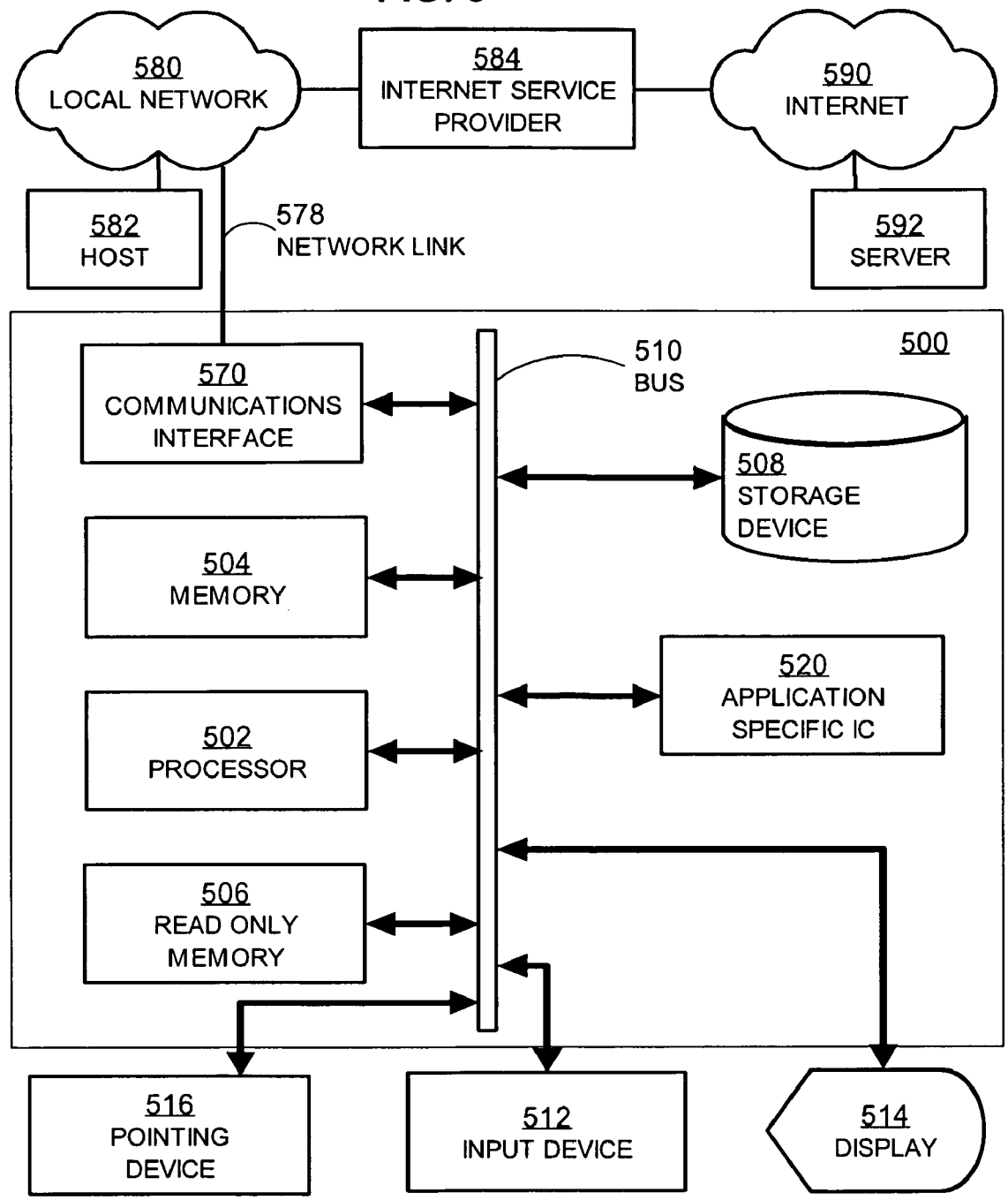
FIG. 5 is a block diagram that illustrates a computer system upon which an embodiment of the invention may be implemented.

FIG. 5 is a block diagram that illustrates a computer system 500 upon which an embodiment of the invention may be implemented. Computer system 500 includes a communication mechanism such as a bus 510 for passing information between other internal and external components of the computer system 500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A series of binary digits constitutes digital data that is used to represent a number or code for a character. A bus 510 includes many parallel conductors of information so that information is transferred quickly among devices coupled to the bus 510. One or more processors 502 for processing information are coupled with the bus 510. A processor 502 performs a set of operations on information. The set of operations include bringing information in from the bus 510 and placing information on the bus 510. The set of operations also typically include comparing two or more units of information, shifting positions of units of information, and combining two or more units of information, such as by addition or multiplication. A series of operations to be executed by the processor 502 constitute computer instructions.

Computer system 500 also includes a memory 504 coupled to bus 510. The memory 504, such as a random access memory (RAM) or other dynamic storage device, stores information including computer instructions. Dynamic memory allows information stored therein to be changed by the computer system 500. RAM allows a unit of information stored at a location called a memory address to be stored and retrieved independently of information at neighboring addresses. The memory 504 is also used by the processor 502 to store temporary values during execution of computer instructions. The computer system 500 also includes a read only memory (ROM) 506 or other static storage device coupled to the bus 510 for storing static information, including instructions, that is not changed by the computer system 500. Also coupled to bus 510 is a non-volatile (persistent) storage device 508, such as a magnetic disk or optical disk, for storing information, including instructions, that persists even when the computer system 500 is turned off or otherwise loses power.

Information, including instructions, is provided to the bus 510 for use by the processor from an external input device 512, such as a keyboard containing alphanumeric keys operated by a human user, or a sensor. A sensor detects conditions in its vicinity and transforms those detections into signals compatible with the signals used to represent information in computer system 500. Other external devices coupled to bus 510, used primarily for interacting with humans, include a display device 514, such as a cathode ray tube (CRT) or a liquid crystal display (LCD), for presenting images, and a pointing device 516, such as a mouse or a trackball or cursor direction keys, for controlling a position of a small cursor image presented on the display 514 and issuing commands associated with graphical elements presented on the display 514.

In the illustrated embodiment, special purpose hardware, such as an application specific integrated circuit (IC) 520, is coupled to bus 510. The special purpose hardware is configured to perform operations not performed by processor 502 quickly enough for special purposes. Examples of application specific ICs include graphics accelerator cards for generating images for display 514, cryptographic boards for encrypting and decrypting messages sent over a network, speech recognition, and interfaces to special external devices, such as robotic arms and medical scanning equipment that repeatedly perform some complex series of operations that are more efficiently implemented in hardware.

Computer system 500 also includes one or more instances of a communications interface 570 coupled to bus 510. Communication interface 570 provides a two-way communication coupling to a variety of external devices that operate with their own processors, such as printers, scanners and external disks. In general the coupling is with a network link 578 that is connected to a local network 580 to which a variety of external devices with their own processors are connected. For example, communication interface 570 may be a parallel port or a serial port or a universal serial bus (USB) port on a personal computer. In some embodiments, communications interface 570 is an integrated services digital network (ISDN) card or a digital subscriber line (DSL) card or a telephone modem that provides an information communication connection to a corresponding type of telephone line. In some embodiments, a communication interface 570 is a cable modem that converts signals on bus 510 into signals for a communication connection over a coaxial cable or into optical signals for a communication connection over a fiber optic cable. As another example, communications interface 570 may be a local area network (LAN) card to provide a data communication connection to a compatible LAN, such as Ethernet. Wireless links may also be implemented. For wireless links, the communications interface 570 sends and receives electrical, acoustic or electromagnetic signals, including infrared and optical signals, that carry information streams, such as digital data. Such signals are examples of carrier waves.

The term computer-readable medium is used herein to refer to any medium that participates in providing information to processor 502, including instructions for execution. Such a medium may take many forms, including, but not limited to, non-volatile media, volatile media and transmission media. Non-volatile media include, for example, optical or magnetic disks, such as storage device 508. Volatile media include, for example, dynamic memory 504. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 578 typically provides information communication through one or more networks to other devices that use or process the information. For example, network link 578 may provide a connection through local network 580 to a host computer 582 or to equipment 584 operated by an Internet Service Provider (ISP). ISP equipment 584 in turn provides data communication services through the public, world-wide packet-switching communication network of networks now commonly referred to as the Internet 590. A computer called a server 592 connected to the Internet provides a service in response to information received over the Internet. For example, server 592 provides information representing video data for presentation at display 514.

The invention is related to the use of computer system 500 for implementing the techniques described herein. According to one embodiment of the invention, those techniques are performed by computer system 500 in response to processor 502 executing one or more series of one or more instructions contained in memory 504. Such instructions, also called software and program code, may be read into memory 504 from another computer-readable medium such as storage device 508. Execution of the series of instructions contained in memory 504 causes processor 502 to perform the method steps described herein. In alternative embodiments, hardware, such as application specific integrated circuit 520, may be used in place of or in combination with software to implement the invention. Thus, embodiments of the invention are not limited to any specific combination of hardware and software.

The signals transmitted over network link 578 and other networks through communications interface 570, which carry information to and from computer system 500, are exemplary forms of carrier waves. Computer system 500 can send and receive information, including program code, through the networks 580, 590 among others, through network link 578 and communications interface 570. In an example using the Internet 590, a server 592 transmits program code for a particular application, requested by a message sent from computer 500, through Internet 590, ISP equipment 584, local network 580 and communications interface 570. The received code may be executed by processor 502 as it is received, or may be stored in storage device 508 or other non-volatile storage for later execution, or both. In this manner, computer system 500 may obtain application program code in the form of a carrier wave.

Various forms of computer readable media may be involved in carrying one or more series of instructions or data or both to processor 502 for execution. For example, instructions and data may initially be carried on a magnetic disk of a remote computer such as host 582. The remote computer loads the instructions and data into its dynamic memory and sends the instructions and data over a telephone line using a modem. A modem local to the computer system 500 receives the instructions and data on a telephone line and uses an infra-red transmitter to convert the instructions and data to an infra-red signal, a carrier wave serving as the network link 578. An infrared detector serving as communications interface 570 receives the instructions and data carried in the infrared signal and places information representing the instructions and data onto bus 510. Bus 510 carries the information to memory 504 from which processor 502 retrieves and executes the instructions using some of the data sent with the instructions. The instructions and data received in memory 504 may optionally be stored on storage device 508, either before or after execution by the processor 502.

4. Extensions and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for determining a duration for administering a treatment with harmful side-effects to a patient with cancer before a hiatus in repeated cycles of treatment duration and hiatus, comprising the steps of:
   determining by a processor an untreated series of measurements that indicate temporal progression of a physical property related to the cancer while the cancer is untreated in a victim outside a population of patients to be treated;
   determining by a processor a treated series of measurements that indicate temporal progression of the physical property of the cancer while a particular multiple dose treatment is administered within a single treatment cycle before a hiatus in treatment, wherein the treated series includes an initial treatment measurement made substantively when the treatment is started and at least two subsequent measurements made at corresponding later times before the hiatus;
   generating by a processor a series of effectiveness values based on the untreated series and the treated series, wherein each effectiveness value indicates a relative value between an untreated time rate of change of the physical property while the cancer is untreated at one time and a treated time rate of change of the physical property while the cancer is treated with the particular treatment at a corresponding time;
   determining a particular elapsed time from start of multiple dose treatment to an earliest time when an effectiveness value reaches a maximum or minimum effectiveness value compared to adjacent effectiveness values; and
   determining a duration for administering the multiple dose treatment to a patient with cancer within a single treatment cycle before a hiatus in treatment based on the particular elapsed time.

2. A method as recited in claim 1, wherein the disease is cancer and the treatment is a chemotherapeutic agent.

3. A method as recited in claim 1, wherein the disease is cancer and the treatment is radiation.

4. A method as recited in claim 1, said step of generating the series of effectiveness values further comprising synchronizing the untreated series and the treated series at a time when the untreated series indicates a value of the physical property that is substantively equal to a value of the physical property at the initial treatment measurement.

5. A method as recited in claim 1, said step of receiving the treated series of measurements further comprising receiving the treated series of measurements that indicate temporal progression of the physical property of the disease while the particular treatment is administered to a particular patient in the population of patients to be treated.

6. A method as recited in claim 1, said step of generating the series of effectiveness values further comprising:
   determining automatically a particular parameter value for a model parameter for a model of the untreated rate of change of the physical property so that the model fits the untreated series of values; and
   determining automatically the untreated rate of change of the physical property at an arbitrary time based on the model and the particular parameter value; and
   determining automatically an effectiveness value based on the untreated rate of change at the arbitrary time.

7. The method as recited in claim 6, wherein:
   the disease is cancer;
   the treatment is a chemotherapy agent;
   the physical property is cancer tumor volume; and
   the model is a Gompertzian model of tumor growth.

8. A method as recited in claim 1, said step of generating the series of effectiveness values further comprising:
   determining automatically a plurality of parameter values for a set of orthogonal functions so that a linear combination of the orthogonal functions with the plurality of parameter values fits the treated series of measurements; and
   determining automatically the treated rate of change of the physical property at an arbitrary time based on a rate of change of the linear combination of the orthogonal functions with the plurality of parameter values; and
   determining automatically an effectiveness value based on the treated rate of change at the arbitrary time.

9. A method as recited in claim 1, said step of determining the elapsed time further comprising:
   determining a first derivative of the series of effectiveness values with respect to time; and
   determining the earliest time when the first derivative crosses zero as the earliest time when an effectiveness value reaches the most effective value.

10. A method as recited in claim 1, wherein:
    each effectiveness value is directly proportional a reduction in an indication of the disease; and
    said step of determining the particular elapsed time further comprises determining the elapsed time from the start of treatment to an earliest time when an effectiveness value reaches a maximum compared to adjacent values.

11. A method as recited in claim 10, wherein:
    the physical property is size of diseased tissue; and
    the effectiveness value is equal to a difference between one and a ratio between the untreated rate of change and the treated rate of change.

12. A method as recited in claim 1, wherein the untreated rate of change varies with changing values of the physical property.

13. A method for treating a patient with cancer, comprising the steps of:
    receiving an untreated series of measurements that indicate temporal progression of a physical property related to cancer while the cancer is untreated in a victim outside a population of patients to be treated;
    receiving a treated series of measurements that indicate temporal progression of the physical property of the cancer while a particular multiple dose treatment is administered within a single treatment cycle before a hiatus in treatment, wherein the treated series includes an initial treatment measurement substantively when the treatment is started and at least two subsequent measurements made at corresponding later times before the hiatus;
    determining a series of effectiveness values based on the untreated series and the treated series, wherein each effectiveness value indicates a relative value between an untreated time rate of change of the physical property while the cancer is untreated at one time and a treated time rate of change of the physical property while the cancer is treated with the particular treatment at a corresponding time;
    determining a particular elapsed time from start of multiple dose treatment to an earliest time when an effectiveness value reaches a maximum or minimum effectiveness value compared to adjacent effectiveness values;

determining, based on the particular elapsed time, a duration for administering the multiple dose treatment to a particular patient with the cancer within a single treatment cycle before a hiatus in repeated treatment cycles of treatment duration and hiatus in treatment based on the elapsed time; and administering the multiple dose treatment to the particular patient for a time that does not exceed the duration within a single treatment during a temporal cycle of treatment and before a hiatus.

14. A method as recited in claim 13, said step of administering the treatment to the particular patient further comprises administering a first dose of the treatment for the duration, wherein the first dose is greater than a second dose of the treatment administered in a different protocol that administers the treatment for a time greater than the duration.

15. A method as recited in claim 13, said step of administering the treatment to the particular patient further comprising repeating said step of administering the treatment after a first hiatus, wherein the first hiatus is less than a second hiatus in a different protocol that administers the treatment for a time greater than the duration.

16. A method for treating a patient with cancer, comprising the step of:

administering, during a temporal treatment cycle of multiple dose treatment and hiatus, a multiple dose treatment to a particular patient for a time that does not exceed a computed duration, wherein the computed duration is determined according to the steps of receiving an untreated series of measurements that indicate temporal progression of a physical property related to cancer while the cancer is untreated in a victim outside a population of patients to be treated;

receiving a treated series of measurements that indicate temporal progression of the physical property of the cancer while a particular multiple dose treatment is administered within a single treatment cycle before a hiatus in treatment, wherein the treated series includes an initial treatment measurement substantively when the treatment is started and at least two subsequent measurements made at corresponding later times before the hiatus;

determining a series of effectiveness values based on the untreated series and the treated series, wherein each effectiveness value indicates a relative value between an untreated time rate of change of the physical property while the cancer is untreated at one time and a treated time rate of change of the physical property while the cancer is treated with the particular treatment at a corresponding time;

determining a particular elapsed time from start of multiple dose treatment to an earliest time when an effectiveness value reaches a maximum or minimum effectiveness value compared to adjacent effectiveness values; and determining, based on the particular elapsed time, the duration for administering the multiple dose treatment to a particular patient with cancer within a single treatment cycle before a hiatus in treatment in repeated cycles of treatment duration and hiatus based on the elapsed time.

17. A nontransitory computer-readable medium carrying one or more series of instructions for determining a duration for administering a treatment with harmful side-effects within one cycle to a patient suffering from cancer before a hiatus in repeated cycles of treatment duration and hiatus, wherein execution of the one or more series of instructions by one or more processors causes the one or more processors to perform the steps of:

receiving an untreated series of measurements that indicate temporal progression of a physical property related to cancer while the cancer is untreated in a victim outside a population of patients to be treated;

receiving a treated series of measurements that indicate temporal progression of the physical property of the cancer while a particular multiple dose treatment is administered within a single treatment cycle before a hiatus in treatment, wherein the second series includes an initial treatment measurement substantively when the treatment is started and at least two subsequent measurements made at corresponding later times before the hiatus;

determining a series of effectiveness values based on the untreated series and the treated series, wherein each effectiveness value indicates a relative value between an untreated time rate of change of the physical property at one time and a treated time rate of change of the physical property at a corresponding time;

determining a particular elapsed time from start of multiple dose treatment to an earliest time when an effectiveness value reaches a maximum or minimum effectiveness value compared to adjacent effectiveness values; and determining, based on the particular elapsed time, a duration for administering the treatment to a patient with cancer within a single treatment cycle before a hiatus in treatment based on the elapsed time.

* * * * *